(12) United States Patent
Blixt et al.

(10) Patent No.: US 10,307,054 B2
(45) Date of Patent: *Jun. 4, 2019

(54) ADAPTIVE CAMERA AND ILLUMINATOR EYETRACKER

(71) Applicant: Tobii AB, Danderyd (SE)

(72) Inventors: Peter Blixt, Hägersten (SE); Gunnar Troili, Täby (SE); Anders Kingbäck, Sigtuna (SE); John Mikael Elvesjö, Stockholm (SE); Märten Skogö, Danderyd (SE)

(73) Assignee: Tobii AB, Danderyd (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/581,548

(22) Filed: Apr. 28, 2017

(65) Prior Publication Data
US 2017/0224211 A1    Aug. 10, 2017

Related U.S. Application Data

(62) Division of application No. 14/563,063, filed on Dec. 8, 2014, now Pat. No. 9,649,029, which is a division
(Continued)

(30) Foreign Application Priority Data

Apr. 1, 2009   (EP) .................................... 09157104

(51) Int. Cl.
*A61B 3/113*   (2006.01)
*A61B 3/00*    (2006.01)
(Continued)

(52) U.S. Cl.
CPC ............ *A61B 3/113* (2013.01); *A61B 3/0008* (2013.01); *A61B 3/0025* (2013.01); *A61B 3/14* (2013.01);
(Continued)

(58) Field of Classification Search
CPC ........... A61B 3/113; A61B 3/145; A61B 3/14; A61B 3/0008; A61B 3/0025; G06T 7/20; G06T 2207/10016; G06K 9/00604
(Continued)

(56) References Cited

U.S. PATENT DOCUMENTS 4,849,906 A    7/1989 Chodos
5,231,674 A    7/1993 Cleveland et al.
(Continued)

FOREIGN PATENT DOCUMENTS

WO    2004030560    5/2004

OTHER PUBLICATIONS

Guestrin, et al. "General Theory of Remote Gaze Estimation Using the Pupil Center and Corneal Reflections" IEEE Transactions on Biomedical Engineering, vol. 53, Nol 6, Jun. 2006; pp. 1124-1133.
(Continued)

*Primary Examiner* — Jordan M Schwartz
(74) *Attorney, Agent, or Firm* — Kilpatrick Townsend & Stockton LLP (57) ABSTRACT

A method includes obtaining an image of an eye in a bright-pupil imaging mode in which a retinal retro-reflection complements the image of the eye in the bright-pupil mode, and obtaining an image of the eye in a dark-pupil imaging mode in which a cornea-scleral retro-reflection complements the image of the eye in the dark-pupil mode. One of the bright-pupil imaging mode and the dark-pupil imaging mode is selected based on quality of obtained images.

20 Claims, 4 Drawing Sheets

Related U.S. Application Data of application No. 13/716,431, filed on Dec. 17, 2012, now Pat. No. 8,944,600, which is a division of application No. 12/752,258, filed on Apr. 1, 2010, now Pat. No. 8,339,446.

(60) Provisional application No. 61/166,012, filed on Apr. 2, 2009.

(51) Int. Cl.
  *A61B 3/14* (2006.01)
  *G06K 9/00* (2006.01)

(52) U.S. Cl.
  CPC .......... *A61B 3/145* (2013.01); *G06K 9/00604* (2013.01)

(58) Field of Classification Search
  USPC .............................. 351/209; 382/103; 396/18
  See application file for complete search history.

(56) References Cited

U.S. PATENT DOCUMENTS

| | | | |
|---|---|---|---|
| 5,604,818 A | 3/1997 | Saitou et al. | |
| 5,818,954 A | 10/1998 | Tomono et al. | |
| 7,401,920 B1 * | 7/2008 | Kranz | A61B 3/113 351/209 |
| 7,522,344 B1 | 4/2009 | Curatu | |
| 7,835,633 B2 | 11/2010 | Omi | |
| 7,863,544 B2 | 1/2011 | Serruys et al. | |
| 8,077,914 B1 | 12/2011 | Kaplan | |
| 8,339,446 B2 | 12/2012 | Blixt et al. | |
| 8,944,600 B2 * | 2/2015 | Blixt | A61B 3/113 351/209 |
| 9,649,029 B2 * | 5/2017 | Blixt | A61B 3/113 |
| 2002/0051116 A1 | 5/2002 | Saarloos et al. | |
| 2003/0058631 A1 | 3/2003 | Yoneda | |
| 2004/0005083 A1 | 1/2004 | Fujimura et al. | |
| 2004/0252277 A1 | 12/2004 | Chmielewski et al. | |
| 2008/0284980 A1 * | 11/2008 | Skogo | A61B 3/113 351/210 |
| 2009/0219386 A1 | 9/2009 | Ebisawa | |
| 2011/0069277 A1 | 3/2011 | Blixt et al. | |
| 2011/0228975 A1 | 9/2011 | Hennessey | |
| 2012/0249957 A1 | 10/2012 | Shibata et al. | |
| 2016/0139665 A1 * | 5/2016 | Lopez | G06F 3/013 345/156 |

OTHER PUBLICATIONS

U.S. Appl. No. 15/595,672, Non-Final Rejection dated Jun. 14, 2018, all pages.

* cited by examiner

Fig. 7 ced application Ser. No. 14/563,063 filed Dec. 8, 2014 which is a divisional appli-
ADAPTIVE CAMERA AND ILLUMINATOR EYETRACKER

RELATED APPLICATIONS

This application is a divisional application of Ser. No. 14/563,063 filed Dec. 8, 2014 which is a divisional application of Ser. No. 13/716,431 filed Dec. 17, 2012, now U.S. Pat. No. 8,944,600, which is a divisional application of Ser. No. 12/752,258 filed Apr. 1, 2010 now U.S. Pat. No. 8,339,446 which claims the benefit of provisional application Ser. No. 61/166,012 filed Apr. 2, 2009 and European application no. 09157104.2 filed Apr. 1, 2009, which are hereby incorporated herein in their entirety by reference.

TECHNICAL FIELD

The present invention relates to a device for illuminating and imaging an eye. More precisely, the invention provides an adaptive pupil-centre-corneal-reflection (PCCR) eye tracking system comprising multiple cameras.

BACKGROUND

A PCCR-based approach to determining the gaze of an eye may use an image of the eye either in its bright-pupil condition (a retinal retro-reflection complements the iris image) or dark-pupil condition (a cornea-scleral reflection complements the iris image). In a given situation, the respective images may be of different quality, and it may even be impossible to carry out an uninterrupted gaze tracking based on just one of these imaging modes. Therefore, to be able to choose the optimal mode, some available eye trackers comprise double reference illuminators for creating the reflections. A first reference illuminator, for use in imaging in the bright-pupil mode, is then arranged coaxially with the optic axis of a camera (image sensor), whereas a second reference illuminator, for use in the dark-pupil mode, is arranged off the camera axis. Such a reference illuminator may be a compound light source arranged round the camera objective in a concentric ring; cf. FIG. 3 in Applicant's patent SE 524003.

It is known in the art (see, e.g., the paper *General Theory of Remote Gaze Estimation Using the Pupil Center and Corneal Reflections* by E. D. Guestrin and M. Eizenmann, *IEEE Transactions on Biomedical Engineering*, Vol. 53, No. 6, pp. 1124-1133 (June 2006), included herein by reference) that the eye's position and orientation, at a given point in time, cannot be unambiguously determined unless the locations of two distinct corneal reflection (or glints, or first Purkinje reflections) can be extracted from one image of the eye or from several, simultaneous images. If two reference illuminators are used simultaneously, however, coexisting glints will mutually blur the measurements by reflections and the like. If the reference illuminators are used alternately (e.g., by time interlacing), then a small time delay will necessarily separate the two images, to the detriment of the accuracy, particularly if the delay falls in the duration of a saccade. The delay also makes the eye tracking slower. A similar drawback becomes noticeable if the bright-pupil image is used for providing an initial guess in the process of finding the location of the pupil centre in the dark-pupil image. This is practiced in the art, as described, notably, in patent application US 2004/0005083. Since the two images cannot be acquired simultaneously, such initial guess is sometimes of little avail.

As many of those skilled in the art will acknowledge, the accuracy of eye tracking is highly dependent on the resolution of the camera used for imaging the eye with the glints. Indeed, the virtual image of the reference illuminator formed by reflection in the cornea is shrunk by a factor 100 or more (assuming a corneal focal length of 4 mm and an illuminator-to-eye distance of at least 400 mm). On the other hand, to avoid serious round-off errors, the image of the reference illuminator should occupy a region of at least, say, ten camera pixels. Hence, for an eye tracker to be useful, a reasonably high performance is required from the camera, which therefore defines a least possible price of the product.

Conventional eye trackers generally perform optimally if the studied person does not move during a measurement session. Particularly annoying are head movements that change the angle between the head and the camera of the eye tracker, because this may introduce obscuring objects into the line of sight from the reference illuminator to the eye or into the line from the eye to the camera. Notably, spectacle frames, eyelashes, eyebrows, nose and protruding brow bones may cause problems of this kind.

It is probably similar considerations that have led to the widespread use of ring-shaped reference illuminators in eye trackers. Conventionally there is a larger ring for providing off-axis illumination and a smaller ring arranged around the circumference of the camera objective to be as coaxial as possible. By surrounding all sides of the camera objective with luminous points, the risk of having the tracked eye obscured is decreased. However, a ring-shaped illuminator is imaged in the cornea as an inhomogeneous spot having lower luminance than a solid light source would. This is detrimental to image contrast and makes it more difficult to find the location of the reflection of the light source. The problem is most severe in the case of the coaxial, smaller illuminator, which is further shrunk by reflection in the convex cornea, as seen above.

In view of the above shortcomings associated with available eye trackers, there appears to be a need for improved eye-tracking devices as regards accuracy, speed, reliability and cost efficiency.

SUMMARY OF THE INVENTION

It is an object of the present invention to provide a device for eye illumination and eye imaging, in a manner suitable for subsequent extraction of gaze-point data from eye images obtained by the device.

In accordance with a first aspect of the invention, an eye tracker is provided which comprises at least one illuminator for illuminating an eye, at least two cameras (or other image sensors) for imaging the eye and a controller. The configuration of the reference illuminator(s) and cameras is such that, firstly, at least one camera is coaxial with a reference illuminator (bright-pupil imaging mode) and, secondly, at least one camera is non-coaxial with a reference illuminator (dark-pupil imaging mode). The controller is adapted to select at least one of the cameras to be active. The camera selection, which is performed repeatedly, is based on an image quality metric which is a function of at least one image quality factor. If one active camera is to be selected, the one which yields the image with the best quality metric is chosen.

In comparison with available devices, an eye tracker according to the invention is less vulnerable to sight-obscuring objects, such as eyelashes and eyebrows, because of the higher probability of one of the two cameras being unhindered. If the line of sight of one camera becomes obscured, the quality-metric value of its image will drop accordingly and the other camera will be considered for activation. Because an illuminator usually dissipates more power than a camera, the invention also represents an energy-economic advantage over available eye trackers.

The invention can be advantageously embodied as an eye tracker comprising two reference illuminators and two cameras, so that four combinations of one illuminator and one camera are possible. One or two combinations will relate to the bright-pupil mode and two or three combinations to the dark-pupil mode (for, as noted above, at least one camera is coaxial with a reference illuminator and at least one is non-coaxial with a reference illuminator). Thus, at least in the dark-pupil mode, if one line of sight becomes obscured, the eye tracker can continue tracking using a different combination in the same mode, which facilitates subsequent image processing such as pupil finding. This makes operation of the eye tracker more reliable.

In an advantageous variation to the previous embodiment, each camera is associated with a coaxial, substantially point-shaped illuminator. Necessarily, this enables two bright-pupil combinations of one camera and one illuminator. A benefit of the point-shapedness of the reference illuminator is that the corneal reflection of the reference illuminator is more likely to appear as a small solid spot with good contrast against the background, so that the location of the reflection can be accurately determined. Because two different camera-illuminator combinations are available, it is not very likely that both are subject to obscuration (which is one of the motives of the ring shape of on-axis reference illuminators of prior art). Generally, a reflection of a reference illuminator covers a spot of several pixels in the camera image, and the location of the reflection, as used herein, refers to the centre of the spot in some suitable sense, as will be detailed below.

Preferably, the eye tracker is operable in a dual-camera mode, in which both cameras are active, which permits truly simultaneous acquisition of images in different illumination conditions. As an economic advantage of this, the resolution requirement on each camera can be relaxed. Since, for instance, the location of a corneal reflection can be determined more accurately when it is imaged by two cameras in distinct positions, the effective accuracy can be retained even though two simpler cameras are used. Assuming the eye tracker is adapted for distances to the viewer in the range up to 1 m, the cameras should be separated by at least 70 mm, i.e., at least 4.0 degrees of arc, if both bright-pupil and dark-pupil imaging is desired. If one available imaging mode is considered sufficient, then the cameras may be arranged closer, such as 50 mm apart.

Any embodiment of the invention may advantageously include operability in an evaluation mode. The evaluation mode has the purpose of assessing the quality and usefulness of a large number of available camera-illuminator combinations. The evaluation mode entails activating a plurality of cameras, while the reference illuminators are sequentially scanned. Alternatively, all cameras are activated during the scan. This expedites the gathering of images for evaluation.

In order not to distract a viewer's attention, the reference illuminators used in any embodiments of the invention are preferably adapted to emit light that is not visible to the human eye. It is advantageous to use light in a wavelength range adjacent to the visible spectrum—thus in the infrared or ultraviolet range—because it may then be possible to use imaging devices for visible light with only minor adaptations. However, it is known that exposure to ultraviolet radiation may be harmful to the human body, so that infrared or near-infrared light is the preferred choice.

As regards the processing of images collected by an eye tracker according to the invention, it is advantageous to use a computational model that includes an aspherical geometric model of the cornea. Preferably, to reflect widely recognised optometric facts, an ellipsoidal cornea model is used. The eye tracker is adapted to determine an orientation of the eye based on the locations of the corneo-scleral reflections of the reference illuminators. The gaze direction of the eye is easily determined once the orientation is known. Because a general ellipsoidal surface is not rotationally symmetric, it may not be necessary for the eye tracker to determine a pupil-centre location and take this into account. While the ellipsoidal shape is common to the majority of persons, the model may need to be fine-tuned according to individual variations in a calibration procedure before measurements are started. The tuneable parameters may include the radius of corneal curvature at the pupil centre and the corneal eccentricity.

In accordance with a second aspect of the invention, there is provided a method for selecting a combination of an active reference illuminator from a plurality of reference illuminators and an active camera from a plurality of cameras. Each camera is adapted to image at least one eye when illuminated by one or more reference illuminators. At least one combination is adapted for imaging in the bright-pupil mode (the camera and the reference illuminator are coaxial) and at least one combination is adapted for imaging in the dark-pupil mode (they are non-coaxial). The method includes the following steps, to be performed in this order:

i) An image quality metric, which depends on at least one image quality factor, is defined.

ii) Two or more eye images are acquired, at least one in the bright-pupil mode and at least one in the dark-pupil mode. The image quality metric is evaluated for each of the images, and the imaging mode which provides the greatest value of the quality metric is selected.

iii) Eye images are acquired using available combinations of an active camera and an active illuminator corresponding to the selected imaging mode, and the image quality metric is evaluated for the images. Preferably, each available camera is included in at least one of the combinations used for acquiring these eye images. That camera which provides the greatest value of the quality metric is selected as active camera.

iv) Once an active camera has been selected, an active reference illuminator remains to be selected. Only a reference illuminator which, in combination with the selected active camera, provides imaging in the selected imaging mode can be chosen. The selection of an active reference illuminator is effected on the basis of the centricity of its corneoscleral reflection (first Purkinje reflection): the illuminator which provides the most centric reflection is selected.

This concludes the initial selection of a combination of an active camera and an active reference illuminator. If the reference illuminators and cameras are provided in an eye tracker operable in an evaluation mode, as set forth above, then advantageously the eye images for which the image quality metric is evaluated are acquired in this mode.

In an advantageous embodiment of the invention, the method for selecting a camera and an illuminator can be complemented with further steps for continually reassessing the selection in an economic and efficient manner. After the above steps have been completed, it is established whether the image quality metric obtained using the selected combination is above or below a predetermined threshold. If it is found to be above the threshold, then step iv) is repeated, that is, it is checked whether the selected reference illuminator actually provides the most centric corneo-scleral reflection or whether switching to some other reference illuminator can improve the centricity. If the image quality factor is found to be below the threshold, the camera selection is revised by repeating step iii). After this, evidently, step iv) has to be repeated. If the image quality metric is still below the threshold even though steps iii) and iv) have been repeated, then the choice of imaging mode is revised by repeating steps ii), iii) and iv).

It is noted that step iv) does not necessarily imply acquiring a set of test images, in which the centricity of the corneo-scleral reflection is evaluated. Indeed, since the spatial configuration of the available reference illuminators is usually known a priori, the switching between different active reference illuminators may be effected based on merely the actual position of the corneo-scleral reflection in the image currently used for eye tracking. E.g., in a situation where the test subject looks to the left, so that the corneo-scleral reflection approaches a right boundary of the cornea, then a reference illuminator located further to the left should be selected instead of the present one. Likewise, if the camera positions are known beforehand, then guidance can be obtained in the camera switching based on the latest eye position and gaze direction. Thus, instead of acquiring test images by each available camera, the cameras most likely to have a better viewing angle are evaluated for selection.

By virtue of its hierarchic nature, the proposed method for updating the selection of a camera-illuminator combination is economical in so far as it limits the number of evaluations of the image quality metric. In a typical computer implementation of the method, this number is likely to influence the computational complexity. The switching between reference illuminators (step iv)) does not require any evaluation of the quality metric. The proposed method also minimises the number of times a camera is temporarily taken out of duty to acquire test images, which interrupts the gaze tracking. This may occur, for instance, when the selection of imaging mode is reassessed (step ii)) by acquiring a test image using the currently active camera and a currently inactive illuminator (one corresponding to the other imaging mode than that currently selected). As regards the reassessment of the camera selection (step iii)), the test images on which the decision is based may be acquired in a dual camera mode, which means that the gaze tracking can be pursued without interruption.

In accordance with a third aspect of the invention, there is provided a computer-program product for causing a general-purpose computer to perform the method for selecting a combination of an active reference illuminator from a plurality of reference illuminators and an active camera from a plurality of cameras, as set forth above.

These and other aspects of the invention will be apparent from and elucidated with reference to the embodiments described hereinafter.

BRIEF DESCRIPTION OF THE DRAWINGS

Embodiments of the present invention will now be described with reference to the accompanying drawings, on which.

DETAILED DESCRIPTION OF EMBODIMENTS

I. Eye Tracker Comprising One Reference Illuminator

Figure 1:
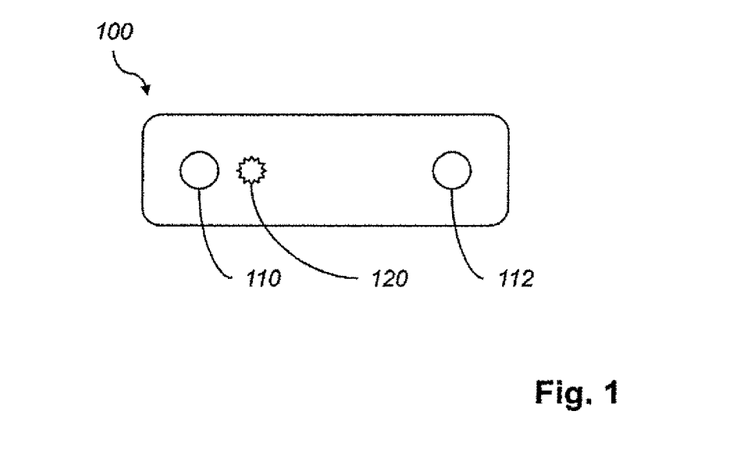
FIG. 1 shows a combined camera and illuminator arrangement in accordance with an embodiment the invention.

FIG. 1 shows a combined camera and illuminator arrangement 100. The arrangement 100 may be part of an eye tracker, in the sense that it is controllable by an eye tracker, and may even be embodied in the same physical unit as such device. It is also envisioned that an eye tracking system may comprise a processor and the arrangement 100 of FIG. 1.

The arrangement 100 comprises a reference illuminator 120 and a first camera 110 provided coaxially with the reference illuminator 120 in the sense that the optic axes of the two devices are parallel and the distance between them is small in relation to the overall length scale. The reference illuminator 120, which preferably is adapted to emit (near) infrared light from a point-shaped aperture, and the first camera 110 are arranged so closely to one another that it is possible to image the retinal retro-reflection (bright-pupil effect) of the reference illuminator 120. In some conditions, this may provide an eye image in which the pupil circumference is resolved with high accuracy. The arrangement 100 further comprises a second camera 112 arranged at such distance away from the reference illuminator 120 that the retinal retro-reflection is not visible. In other words, the second camera 112 is adapted to image the eye in its dark-pupil condition. The reference illuminator 120 of the arrangement 100 is located between the cameras 110, 112, but may also, in an alternative embodiment, be located to the right or left of the cameras 110, 112.

When the arrangement 100 is used in eye tracking, the reference illuminator 120 and at least one of the cameras are active. (Two active cameras may be required in an initial regime of the eye tracking for determining the spatial position of the eye; in eye trackers comprising plural illuminators a single image in which two reflections appear may be sufficient to achieve the same result.) The choice of active camera—and equivalently, the choice between imaging in the bright-pupil or dark-pupil mode—depends on the actual image quality obtained using each camera, as outlined above. The image quality metric, which may be determined by an external processing means, may take several quality factors into account, as will be further discussed in section IV below.

The arrangement 100 may be operable in a dual-camera mode, which improves the accuracy in finding the glint. Referring to the paper by Guestrin and Eizenmann's paper (see above), the extra information obtained by the second camera is added as more rows added into equation system (18), which will be solved to give the centre of corneal curvature c. The added rows will imply that the centre of corneal curvature is determined with greater accuracy. In exceptional cases—e.g., when the spatial configurations of the cameras is unfortunate—the addition of rows may actually lead to an increased condition number of the matrix; then the single-camera mode may be temporarily resumed.

To find the position of an eye, one may determine the location of an illuminator (the world coordinate of which is a priori known) relative to the eye by considering its cornea-scleral reflection. When a single camera is used, the illuminator location $X_{ill}$ may be computed as an average weighted by the intensities:

$$X_{ill} = \frac{\sum_{i \in G} X_i \times \text{INT}_i}{\sum_{i \in G} \text{INT}_i}.$$

Here G is a set of pixels in the image in which the glint is contained, $\text{INT}_i$ is the intensity (after subtraction by the background intensity) of the ith pixel, and $X_i$ is the world coordinate of a light source that gives a corneo-scleral reflection in the ith pixel. However, when two cameras are used, the calculation can be refined as follows:

$$X_{ill} = \frac{\sum_{i \in G} X_i \times \text{INT}_i + \sum_{i \in H} X_i \times \text{INT}_i}{\sum_{i \in G} \text{INT}_i + \sum_{i \in H} \text{INT}_i}$$

where G is a set of pixels of the first camera's image containing the glint, and H is a set of pixels of the second camera's image containing the glint. By linearity, assuming the two cameras are of identical type, the standard deviation of the estimation of $X_{ill}$ decreases by a factor of up to $1/\sqrt{2}$ if the dual-camera equation is used instead of the single-camera equation.

II. Eye Tracker Comprising Plural Reference Illuminators

Figure 2:
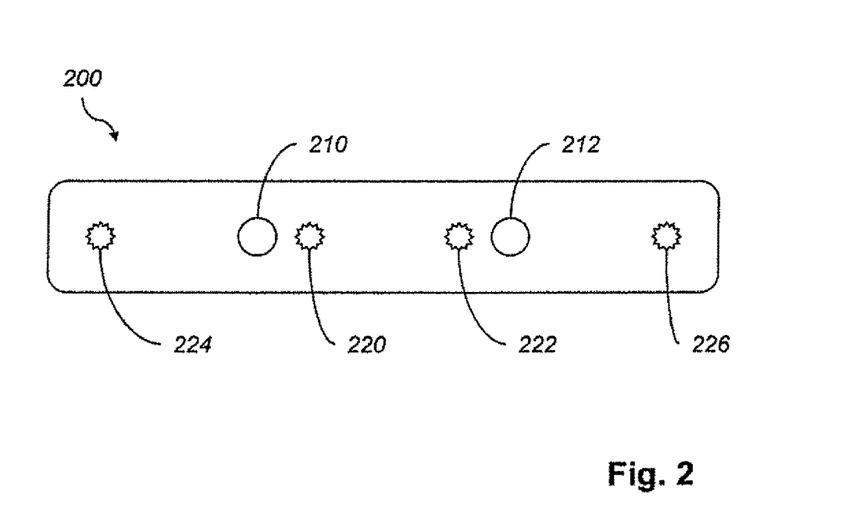
FIG. 2 shows a combined camera and illuminator arrangement in accordance with another embodiment of the invention.

FIG. 2 shows a combined camera and illuminator arrangement 200. Just like the arrangement 100 of FIG. 1, it comprises first and second cameras 210, 212. However, the present arrangement 200 is equipped with four reference illuminators 220-226. A first reference illuminator 220 of these is coaxial with the first camera 210 and a second reference illuminator 222 is coaxial with the second camera 212. The cameras 210, 212 are situated some distance apart, so that the first reference illuminator 220 is non-coaxial with the second camera 212 and the second reference illuminator 222 is non-coaxial with the first camera 210. The least distance at which non-coaxiality (the cease of the bright-pupil effect) occurs is dependent on the distance from the arrangement 200 to the eye, the actual pupil diameter and various parameters that are subject to individual variation. Typically, if the arrangement 200 is designed for measurements on eyes not further away than 1 m, then a separation of the cameras by 100 mm may be considered sufficient. The third and fourth reference illuminators 224, 226, which are respectively arranged on the left and right side of the arrangement 200, are suitably active at large lateral gaze angles. This way, a centrally located glint can be obtained also at these angles.

Figure 3:
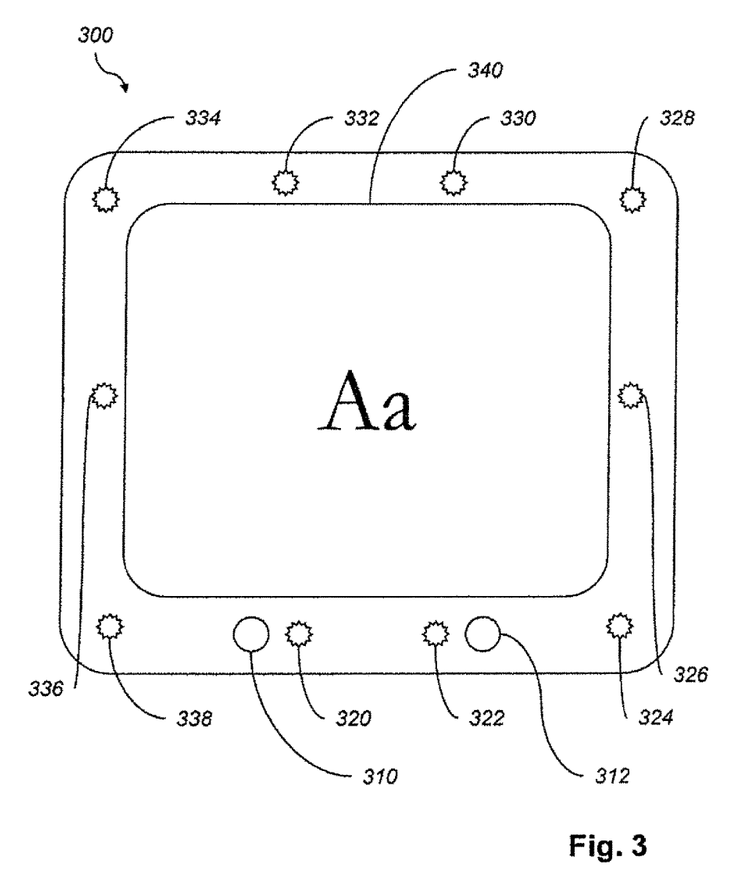
FIG. 3 shows a combined camera and illuminator arrangement in accordance with a further embodiment of the invention.

FIG. 3 depicts another embodiment of a combined camera, illuminator and visual display arrangement 300. The reference illuminators and cameras of the arrangement 300 are provided around the edge of a screen surface 340 for displaying graphical information. In contrast to the arrangements shown in FIG. 2, in which the reference illuminators are aligned one-dimensionally, the present arrangement 300 comprises reference illuminators 320-338 having a two-dimensional configuration. Not only does this increase the range of gaze angles for which a central corneal glint can be achieved. It also enables assessments of mappings involving angular deformations or differing horizontal and vertical deformations. For instance, reflection in a surface having two different radii of curvature, notably an elliptic surface, will deform a square into a rectangle or a parallelogram. By assessing the ratio of the horizontal and vertical length scales under the reflection, information relating to the reflection point on the surface can be obtained. By studying how the different angles change under the reflection, it is possible to estimate the skewness of the surface around the reflection point.

III. PCCR Gaze Tracking Using an Aspherical Corneal Model

Figure 5:
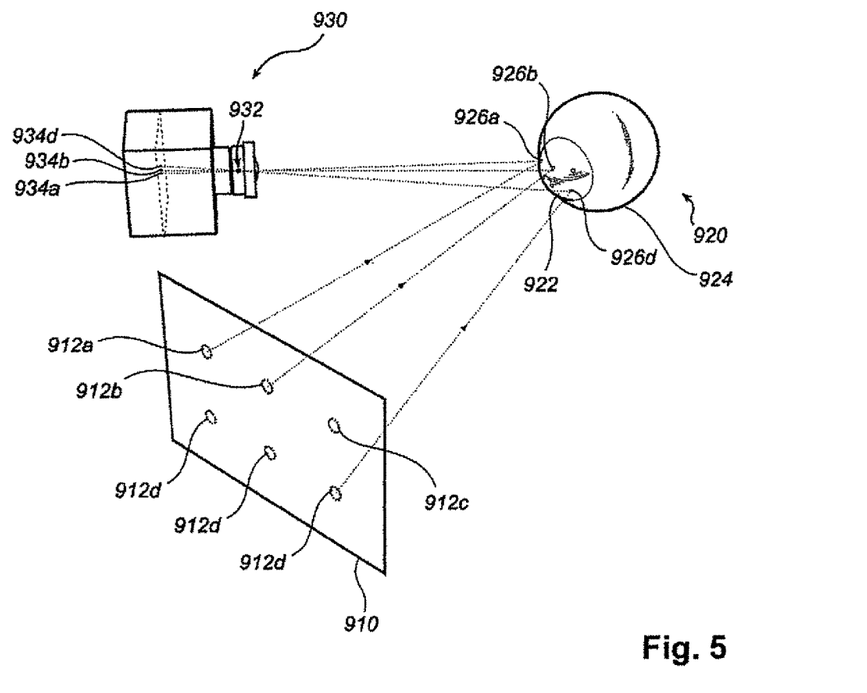
FIG. 5 is a diagrammatic perspective drawing showing an array of reference illuminators, their corneo-scleral reflection and a camera device adapted to image the eye with said reflection.

Gaze tracking using an aspherical cornea model, more particularly an ellipsoidal cornea model, will now be outlined. FIG. 5 diagrammatically depicts the experimental situation. Reference illuminators 912, each of which is independently activable, are provided in an object plane 910. The illuminators 912 are imaged as corneal reflections 926 in the cornea 922 or sclera 924 of a person's eye 920. A camera 930, which is preferably a digital imaging device, images the corneal reflections 926 as image points 934. In a simplified model, as shown on the drawing, the imaging of the camera 930 is determined by a (rear) nodal point 932 and an image plane. For clarity, light rays are indicated from reference illuminators 912a, 912b and 912d only. The compound imaging process of the cornea 922 and the camera 930, which maps each reference illuminator 912 to an image point 934, can be expressed by the following mathematical relationship:

$$X' = [\text{Proj} \circ \text{Refl}_{T(E)}](X),$$

where

Proj is a perspective projection (which in homogeneous coordinates is a linear mapping) known through camera calibration;

E is an ellipsoid representing the corneal surface, known through personal calibration of the test subject while focusing sample points;

T is a rigid transformation which reflects the actual position and orientation of the ellipsoid;

X is a coordinate vector for an illuminator known through the predetermined illuminator arrangement; and X' is a coordinate vector for the camera image of the same illuminator.

The reflection map $\text{Refl}_{T(E)}$ (which is determined by the assumptions of rectilinear propagation of light and of equality between angles of incidence and reflection; in computer-graphics terminology it is an 'environment map') depends parametrically on T(E) which, in turn, is a function of the actual position and orientation T of the cornea. When T(E) is found, such that $$\text{Proj}^{-1}(X') = \text{Refl}_{T(E)}(X)$$

holds true (this equation is equivalent to the previous one), the position and orientation of the eye are known, and the gaze vector can be determined in a straightforward manner. The parameters specifying the mappings Proj and $\text{Refl}_{T(E)}$ can be estimated by considering pairs of known object and image points (X,X'), preferably the reference illuminators and their images under reflection in the cornea. Once the mappings are known, it is possible to find counterparts of object points in the image and vice versa; particularly, the location of the pupil centre can be mapped to the image to provide an approximate gaze point.

Figure 4:
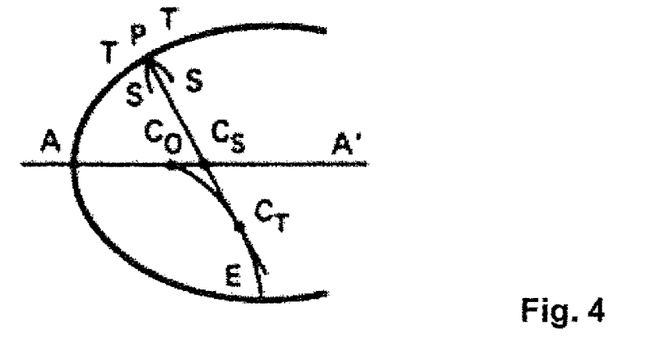
FIG. 4 is a diagrammatic cross-sectional view of the cornea.

A procedure of solving the gaze-detection problem will now be outlined; one of its advantages over gaze detection via a complete estimation of the mappings Proj and $\text{Refl}_{T(E)}$ is that sufficient information for finding the gaze-point may be obtained with fewer computations and less input data. The ellipsoid E used to model the cornea is more precisely given as a surface of revolution, with respect to the x axis, of the curve $$y^2 = 2r_0 x - p x^2 \Leftrightarrow \left(\frac{x - r_0/p}{r_0/p}\right)^2 + \left(\frac{y}{r_0/\sqrt{p}}\right)^2 = 1,$$

where p<1 (the ellipsoid is prolate), x is the dorso-ventral coordinate and y is the vertical coordinate. An ellipsoid having this shape is shown in FIG. 4, wherein the line AA' represents the x axis and the y direction is vertical on the drawing. In a three-dimensional description, if a lateral coordinate z is included, E is defined by $$\left(\frac{x - r_0/p}{r_0/p}\right)^2 + \left(\frac{y}{r_0/\sqrt{p}}\right)^2 + \left(\frac{z}{r_0/\sqrt{p}}\right)^2 = 1.$$

The arc SPS in FIG. 4 represents the sagittal radius of curvature, which is given by $$r_S(y) = \sqrt{r_0^2 + (1-p)y^2},$$

where y is the height coordinate of point P. The tangential radius of curvature, as measured on the arc TPT in the plane of the drawing, is defined as $$r_T(y) = \frac{r_S(y)^3}{r_0^2}.$$

Points $C_S$ and $C_T$ are the respective centres of sagittal and tangential curvature at P. Because E is a surface of revolution, A:(0,0) is an umbilical point, at which both radii of curvature are equal to the minimal radius $r_0$. The described model is valid in the corneal portion of the eye, whereas the sclera has an approximately spherical shape. Typical values of the minimal radius and the eccentricity are $r_0$=7.8 mm and p=0.7, but vary between individual corneae. To achieve optimal accuracy, these constants may be determined for each test subject in a calibration step prior to the gaze tracking. The calibration step may also include determining the distance from the pupil centre to the corresponding centre $C_0$ of corneal curvature and the angular deviation between the visual and optic axes of the eye. It is noted that the spherical model is obtained as a special case by setting p=1 in the formulas above; as an immediate consequence hereof, the sagittal and tangential radii are equal.

The calculations may be carried out along the lines of the already cited article by Guestrin and Eizenmann, however with certain modifications to account for the aspherical cornea model. Following Guestrin and Eizenmann, the locus of a reference illuminator 912 is denoted by L, the nodal point 932 of the camera is denoted by O and the image 934 of the corneal reflection is denoted by U. Because each point P≠A on the cornea has two different radii of curvature in the ellipsoidal model, the article's co-planarity assumption of vectors $\overrightarrow{LO}, \overrightarrow{OU}, \overrightarrow{OC_0}$, by which notably each line of equation 15 follows, is no longer valid. In the case of an ellipsoidal cornea model, separate equations are obtained for the tangential and sagittal components of the vectors. Separating $\overrightarrow{OU}, \overrightarrow{LO}$ in sagittal and tangential components by orthogonal projection, as per $$\overrightarrow{OU} = \overrightarrow{v_S} + \overrightarrow{v_T},$$

$$\overrightarrow{LO} = \overrightarrow{w_S} + \overrightarrow{w_T},$$

the following groups of co-planar vectors are obtained: $\overrightarrow{C_S P}, \overrightarrow{v_S}, \overrightarrow{w_S}$ and $\overrightarrow{C_T P}, \overrightarrow{v_T}, \overrightarrow{w_T}$. The calculations can then be continued in a manner similar to that disclosed in the article.

The inventors have found empirically that use of an ellipsoidal cornea model leads to a significant increase in accuracy. It has even been observed that pupil-centre tracking is in some cases not necessary as a supplement to glint tracking, as practised hitherto in the art. Indeed, tracking of the cornea—apprehended as an ellipsoidal, rotationally asymmetric surface—provides sufficient information (apart from calibration data such as the angular difference between the optic axis and the visual axis) that the orientation of the eye can be determined. Likewise, the process of calibrating certain parameters, notably the minimal radius of curvature and the eccentricity, can be simplified in so far as the test subject is not required to fix his or her eyes on training points. Such improvement of the calibration process is dependent on the correctness of the assumption that the optic axis of the eye coincides with the symmetry axis AA'. Further improvements may be achieved by using a compound light pattern or a time-varying light pattern for generating corneo-scleral glints.

IV. Method for Selecting a Combination of a Camera and a Reference Illuminator

Figure 6:
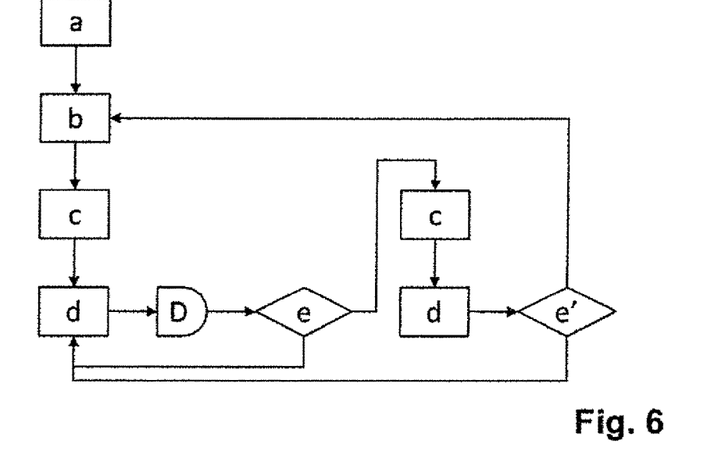
FIG. 6 is a flowchart of the method for selecting a combination of a camera and a reference illuminator according to an embodiment the invention.

With reference to FIG. 6, a preferred embodiment of a method for selecting a combination of an active camera and an active reference illuminator will be described. The selection is made from a plurality of reference illuminators adapted to illuminate at least one eye and a plurality of cameras adapted to image the eye or eyes with the aim of selecting that combination which provides the most suitable conditions for gaze tracking of the eye(s).

In step a) of the method, an image quality metric is defined. The image quality metric may be based on the quality factors indicated in table 1 below.

TABLE 1

| Image quality factors | |
|---|---|
| NbrPupils | The number of pupils detected by the camera. Two detected pupils are preferred to one or none. |
| GazeDetNoise | If the test subject fixates a number of visible points in a calibration process, then parameters can be set to such values that the expected divergence from the true point locations is zero. The gaze-detection noise after this process can be expressed as a statistical measure (such as variance, standard deviation, maximal value etc.) of the divergence. A lower gaze-detection noise is preferred. |

TABLE 1-continued

Image quality factors

| | |
|---|---|
| PupilContrast | The difference in luminance of a region of the pupil and a region of the iris. Preferably, the regions are located centrally in the pupil and the iris, respectively, and the luminance values are averaged over the regions. A greater pupil contrast is preferred. |
| IrisGradient | Off-axis regions in a camera's field of view may have a lower (effective) resolution than central regions. The magnitude of the gradient at the pupil-iris boundary is taken as a measure of the resolution. A greater magnitude of the gradient is preferred. |
| Obstacles | The pupil-iris boundary may be obscured by the presence of obstacles, such as eyelashes, non-transparent parts of eye glasses, reflections from eye-glass lenses, glints, eyebrows, nose and the like. It is noted that the most centric glint may lie on the pupil-iris boundary and be detrimental to the pupil finding; in such circumstances, it may be better to use the illuminator that gives the next most centric glint. The absence of obstacles is preferred. |
| SNR | A signal-to-noise ratio can be defined by taking PupilContrast (see above) as a measure of the signal intensity and the standard deviation at the centre of the pupil, which is a normally a monochrome region, as a measure of the noise. A higher signal-to-noise ratio is preferred. |

Out of these quality factors, the inventors deem NbrPupils, GazeDetNoise and PupilContrast to be the most important, whereas IrisGradient, Obstacles and SNR may be used as additional factors. The image quality factors may be combined into a total quality metric as per:

image Quality=$\alpha_1$NbrPupils+$\alpha_2$GazeDetNoise+
$\alpha_3$PupilContrast+$\alpha_4$IrisGradient+$\alpha_5$Obstacles+
$\alpha_6$SNR, where coefficients $\alpha_1, \alpha_2, \ldots, \alpha_6$ are constants of appropriate signs. For instance, $\alpha_1$ and $\alpha_2$ should be of opposite signs, considering the preferred values of the quantities. Since the image quality metric is only used for establishing the relative quality of two images, there is no real need for an absolute calibration of the sub-metric. However, the relative weighting between sub-metrics, as reflected by the absolute values of the coefficients, should be chosen with some care to fit the requirements of the application.

The possible combinations of a camera and an illuminator fall into two groups: combinations of two coaxial components and combinations of two non-coaxial components. The combinations of coaxial components are adapted to image the eye(s) in the bright-pupil mode (a retinal retro-reflection complements the iris image), whereas the combinations of non-coaxial components are adapted to image in the dark-pupil mode (a corneoscleral reflection complements the iris image). Step a) is followed by step b), in which either the bright-pupil or the dark-pupil imaging mode is selected. To this end, at least one image of the eye in the dark-pupil mode and at least one in the bright-pupil mode are acquired. The comparison is more accurate if these at least two images are acquired closely in time, which also makes the selection process swifter. To maximise both these benefits, the images are acquired simultaneously if possible (that is, if only one bright-pupil image is taken) in this embodiment. Preferably, the images are acquired simultaneously. The image quality metric is evaluated for these images, and the imaging mode is selected in accordance with the highest value of the metric. If more than one image has been acquired in each mode, then the imaging mode of the image having the globally maximal quality metric is selected.

Upon completion of step b), the method proceeds to step c), wherein an active camera is selected. The image quality metric is evaluated for images acquired using combinations according to the selected imaging mode. Possibly, some images which were used in step b) may be used again. The winning quality metric value determines which camera is selected. In this step, just like in step b), the images for which the image quality factor is assessed may be acquired while the device is in an evaluation mode.

It remains to select, in step d), an active reference illuminator to be used in combination with the selected active camera. An advantageous way of finding the most suitable reference illuminator is as follows: using an initially selected reference illuminator the corneo-scleral reflection is retrieved; the deviation from the pupil centre of the reflection is established; it is determined whether there is an alternative reference illuminator which has such position in relation to the initially selected illuminator (is located in a direction opposite the deviation) that a more centric corneo-scleral reflection can be achieved; if such alternative reference illuminator is available, it is selected and the centricity of the corneoscleral glint is reassessed; if no improvement to the centricity is achieved using the alternative reference illuminator, reversion to the initially selected reference illuminator takes place. This procedure may be refined by taking into account the magnitude of the reflection's deviation from the pupil centre; for instance, a relatively small deviation may not motivate use of an alternative reference illuminator.

On completion of step d), a combination of an active reference illuminator and an active camera has been selected. The centricity of the corneo-scleral reflection (step d)) is reassessed regularly, and this may provoke a decision to switch to another reference illuminator. To avoid too frequent reassessment of the centricity, a delay D of suitable duration (which the skilled person should be able to determine by routine experimentation) is provided between repetitions of step d). The delay causes an intermittent repetition of step d). Choosing a longer delay D eases the computational load, but deteriorates the accuracy of the eye tracker. It is also possible to provide a delay D with adaptive duration, which reflects empirically observed human eye-movement patterns, such as saccadic movements. To maintain a high image quality, the image quality metric is evaluated for the selected combination, in step e), at regular intervals (such as after every completion of step d) or after every $2^{nd}$, $5^{th}$, $10^{th}$ or $20^{th}$ completion). If the image quality is greater than or equal to a predetermined level, then the intermittent repetition of step d) is resumed. If however the image quality metric is below the predetermined level although updating of the reference illuminator selection (step d)) has been effected, then the camera selection is revised by repeating steps c) and d). Immediately after such repetition, in step e'), the image quality metric is evaluated again. If the image quality metric is still below the predetermined level, then the selection of imaging mode is revised by repeating steps b), c) and d); otherwise, the method resumes the intermittent repetition of step d).

Figure 7:
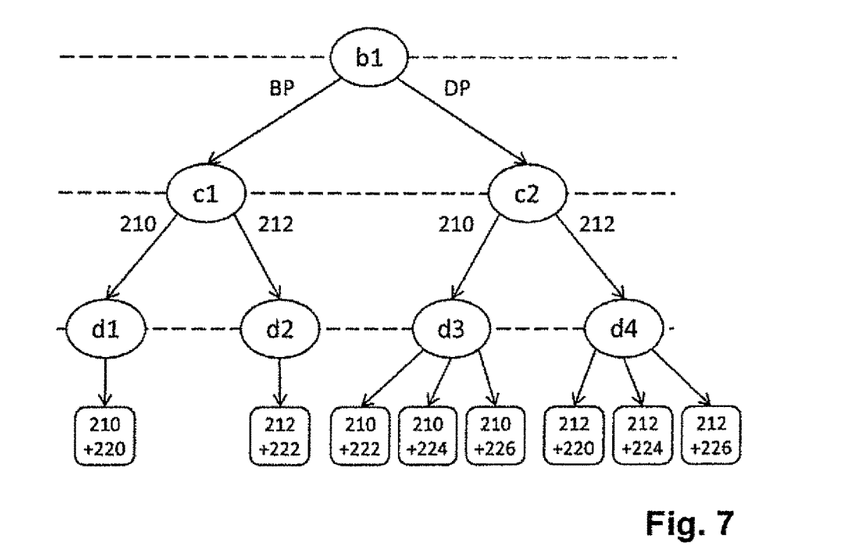
FIG. 7 is an illustration of a decision tree associated with the method for selecting a combination of a camera and a reference illuminator when applied to the combined camera and illuminator arrangement of FIG. 2.

With reference to FIG. 7, an application of the described method to the arrangement 200 shown in FIG. 2 will now be outlined. The arrangement 200 comprises first and second cameras 210, 212 and first, second, third and fourth reference illuminators 220, 222, 224 and 226. The combination of camera 210 and illuminator 220 is coaxial, as is the combination of camera 212 and illuminator 222. The other six combinations are non-coaxial. The decisions taken during execution of the method are illustrated in the form of a tree in FIG. 7. Nodes b1, c1, c2, d1, d2, d3 and d4 symbolise decision points; an arrow symbolises a decision to select an imaging mode (on the top level), a camera (on the middle level) or an illuminator (on the lowest level); and the leaves symbolise a complete combination of an active camera and an illuminator, as indicated.

Assuming an image quality metric has been defined the first decision point b1 is whether to use the bright-pupil (BP) or dark-pupil (DP) imaging mode. If the bright-pupil mode is chosen, the method moves to decision point c1, at which the most suitable of the first camera 210 and the second camera 212 is selected. No more decision is taken if the first camera 210 is selected, for only the first illuminator 220 is coaxial with the first camera 210, and likewise, a selection of the second camera 212 inevitably implies that the combination with the second illuminator 222 will be used. Hence, decision points d1 and d2 are trivial. If instead the dark-pupil mode is selected (at decision point b1), each choice of an active camera (at decision point c2) leads to a choice of three possible reference illuminators (at each of decision points d3 and d4). When the method has reached one of the leaves in the decision tree, the initial selection of a camera-illuminator combination is complete.

The selection is updated by climbing one level up in the tree. As noted, the selection of a reference illuminator is trivial in the case of bright-pupil imaging, but at decision point d3 for instance, there is a choice between the second, third and fourth illuminators 222, 224, 226. The second illuminator 222 is likely to give the most centric corneal reflection for tracking a central gaze direction, whereas the third and fourth illuminators 224, 226 are probably suitable for lateral gaze directions. The switching may be performed by a simple control mechanism. If evaluation of the image quality metric reveals that updating of the active illuminator selection cannot provide sufficient image quality, the middle decision level is resumed (backwards along the arrows of the decision tree) and possibly the top level as well, should the image quality not have improved sufficiently.

V. Closing Remarks

While the invention has been illustrated and described in detail in the drawings and foregoing description, such illustration and description are to be considered illustrative or exemplary and not restrictive; the invention is not limited to the disclosed embodiments. For example, the spatial arrangement of the reference illuminators can be varied as well as their number, and the image quality metric can be adapted to the preferences of the intended users of each particular embodiment.

Other variations to the disclosed embodiments can be understood and effectuated by those skilled in the art in practicing the claimed invention, from a study of the drawings, the disclosure, and the appended claims. In the claims, the word 'comprising' does not exclude other elements or steps, and the indefinite article 'a' or 'an' does not exclude a plurality. A single processor or other unit may fulfil the functions of several items received in the claims. The mere fact that certain measures are recited in mutually different dependent claims does not indicate that a combination of these measured cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method comprising:
   obtaining a first image of an eye in a bright-pupil imaging mode, the first image comprising a retinal retro-reflection;
   obtaining a second image of the eye in a dark-pupil imaging mode, the second image being different from the first image and comprising a corneo-scleral retro-reflection; and
   selecting, based on a comparison of a first quality of the first image and a second quality of the second image, one of the bright-pupil imaging mode and the dark-pupil imaging mode;
   tracking, by an eye tracker, the eye based on the selected imaging mode.

2. The method according to claim 1, wherein the selected imaging mode corresponds to the one of the obtained images of highest quality.

3. The method according to claim 1, further comprising evaluating the quality of at least one image obtained during the tracking of the eye and revising the selection of the imaging mode based on the evaluation.

4. The method according to claim 1, further comprising selecting at least a camera for performing the tracking of the eye in the selected imaging mode.

5. The method according to claim 4, further comprising selecting a reference illuminator, which in combination with the selected camera, provides the selected imaging mode.

6. An eye tracker controller comprising:
   a processor configured to:
      obtain a first image of an eye in a bright-pupil imaging mode, the first image comprising a retinal retro-reflection,
      obtain a second image of the eye in a dark-pupil imaging mode, the second image being different from the first image and comprising a corneo-scleral retro-reflection, and
      select, based on a comparison of a first quality of the first image and a second quality of the second image, one of the bright-pupil imaging mode and the dark-pupil imaging mode; tracking, by an eye tracker, the eye based on the selected imaging mode.

7. The eye tracker controller according to claim 6, wherein the selected imaging mode corresponds to the one of the obtained images of highest quality.

8. The eye tracker controller according to claim 6, wherein said processor is further configured to evaluate the quality of at least one image obtained during the tracking of the eye, and revise the selection of the imaging mode based on the evaluation.

9. The eye tracker controller according to claim 6, wherein said processor is further configured to select at least a camera for providing the selected imaging mode.

10. The eye tracker controller according to claim 9, wherein said processor is further configured to select a reference illuminator, which in combination with the selected camera, provides the selected imaging mode.

11. An eye tracker comprising:
    a plurality of cameras for imaging an eye, with at least one camera being arranged to image the eye in a bright-pupil imaging mode, and with at least one other camera being arranged to image the eye in a dark-pupil imaging mode; and a controller configured to:
obtain a first image of the eye in the bright-pupil imaging mode, the first image comprising a retinal retro-reflection,
obtain a second image of the eye in the dark-pupil imaging mode, the second image being different from the first image and comprising a corneo-scleral retro-reflection, and
select, based on a comparison of a first quality of the first image and a second quality of the second image, one of the bright-pupil imaging mode and the dark-pupil imaging mode; tracking, by an eye tracker, the eye based on the selected imaging mode.

12. The eye tracker according to claim 11, wherein the selected imaging mode corresponds to the one of the obtained images of highest quality.

13. The eye tracker according to claim 11, wherein said controller is further configured to evaluate the quality of at least one image obtained during the tracking of the eye, and revise the selection of the imaging mode based on the evaluation.

14. The eye tracker according to claim 11, wherein said controller is further configured to select at least one of said plurality of cameras corresponding to the selected imaging mode to track the eye.

15. The eye tracker according to claim 14, further comprising at least one reference illuminator for illuminating the eye, and wherein said controller is further configured to select said at least one reference illuminator, which in combination with said at least one selected camera, provides the selected imaging mode.

16. A computer-program product comprising computer-readable instructions, which when executed on a general-purpose computer, causes an eye tracker to perform the following:
obtaining a first image of an eye in a bright-pupil imaging mode, the first image comprising a retinal retro-reflection;
obtaining a second image of the eye in a dark-pupil imaging mode, the second image being different from the first image and comprising a corneo-scleral retro-reflection; and
selecting, based on a comparison of a first quality of the first image and a second quality of the second image, one of the bright-pupil imaging mode and the dark-pupil imaging mode; tracking, by an eye tracker, the eye based on the selected imaging mode.

17. The computer-program product according to claim 16, wherein the selected imaging mode corresponds to the one of the obtained images of highest quality.

18. The computer-program product according to claim 16, further causes the eye tracker to evaluate the quality of at least one image obtained during the tracking of the eye and revise the selection of the imaging mode based on the evaluation.

19. The computer-program product according to claim 16, further causes the eye tracker to select at least a camera for performing the tracking of the eye in the selected imaging mode.

20. The computer-program product according to claim 19, further causes the eye tracker to select a reference illuminator, which in combination with the selected camera, provides the selected imaging mode.

* * * * *